(12) United States Patent
Kerboul et al.

(10) Patent No.: US 9,744,013 B2
(45) Date of Patent: Aug. 29, 2017

(54) MEDICAL DEVICE TRAY AND METHOD OF FORMING THE MEDICAL DEVICE TRAY

(71) Applicant: Symmetry Medical Manufacturing, Inc., Warsaw, IN (US)

(72) Inventors: Guillaume Kerboul, Crudwell (GB); James Truscott, Swindon (GB); Benjamin Dassonville, Brignoud (FR); Antoine Warocquier, Bondues (FR)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 0 days.

(21) Appl. No.: 14/592,311

(22) Filed: Jan. 8, 2015

(65) Prior Publication Data

US 2015/0122682 A1    May 7, 2015

Related U.S. Application Data

(63) Continuation-in-part of application No. 14/157,811, filed on Jan. 17, 2014.

(30) Foreign Application Priority Data

Jan. 23, 2013  (EP) .................................... 13000344

(51) Int. Cl.
*B65D 83/10*    (2006.01)
*A61C 19/02*    (2006.01)
(Continued)

(52) U.S. Cl.
CPC .............. *A61C 19/02* (2013.01); *A61B 50/20* (2016.02); *A61B 50/24* (2016.02); *A61B 50/33* (2016.02);
(Continued)

(58) Field of Classification Search
CPC ......... B65D 25/108; A61C 3/04; A61C 19/02; A61B 50/20; A61B 50/33; A61B 50/24; Y10T 29/49826
(Continued)

(56) References Cited

U.S. PATENT DOCUMENTS 2,119,832 A * 6/1938 Schless ..................... A47F 7/02
                                                    206/486
2,971,637 A    2/1961 Simons
(Continued)

FOREIGN PATENT DOCUMENTS

WO    2014162272 A1    10/2014

OTHER PUBLICATIONS

Extended European Search Report dated May 12, 2016 for European Application No. 16 15 0381 (10 pages).

*Primary Examiner* — Luan K Bui
(74) *Attorney, Agent, or Firm* — Taylor IP, P.C.

(57) ABSTRACT

A medical device tray for carrying a plurality of medical devices includes: a base made of a substantially rigid material, the base forming at least one base through-hole that has an associated visual indicator; and a covering affixed to the base, the covering being made of a material which is softer than the substantially rigid material of the base and substantially transparent, the covering forming at least one covering through-hole, the at least one base through-hole and the at least one covering through-hole cooperating to form at least one medical device tray through-hole configured for directly supporting a respective one of the plurality of medical devices.

12 Claims, 8 Drawing Sheets

(51) Int. Cl.
  *B65D 25/10* (2006.01)
  *B65D 25/54* (2006.01)
  *A61C 3/04* (2006.01)
  *A61B 50/20* (2016.01)
  *A61B 50/24* (2016.01)
  *A61B 50/33* (2016.01)

(52) U.S. Cl.
  CPC .............. *A61C 3/04* (2013.01); *B65D 25/108* (2013.01); *B65D 25/54* (2013.01); *Y10T 29/49826* (2015.01)

(58) Field of Classification Search
  USPC ...... 206/63.5, 363, 368, 369, 370, 372, 484, 206/497, 560, 562, 563, 565, 459.5, 206/484.1, 484.2; 211/85.13, 60.1, 70.6
  See application file for complete search history.

(56) References Cited

U.S. PATENT DOCUMENTS

| | | | |
|---|---|---|---|
| 3,469,687 A | 9/1969 | Schneider | |
| 3,947,620 A * | 3/1976 | Plant ...................... | B32B 27/00 220/2.1 A |
| 4,191,291 A | 3/1980 | Brown | |
| 4,253,830 A * | 3/1981 | Kazen ..................... | A61C 3/04 206/368 |
| 4,256,457 A | 3/1981 | Behring | |
| 4,503,972 A | 3/1985 | Nelligan et al. | |
| 4,669,416 A * | 6/1987 | Delgado ................. | B05C 13/02 118/500 |
| 4,928,821 A * | 5/1990 | Belko, Jr. .............. | H01G 13/00 206/486 |
| 5,340,551 A | 8/1994 | Berry, Jr. | |
| 5,358,112 A | 10/1994 | Gardner | |
| 5,377,823 A * | 1/1995 | Steen .................... | A61C 19/005 206/63.5 |
| 5,525,314 A * | 6/1996 | Hurson ................... | A61C 3/04 206/369 |
| 5,743,734 A | 4/1998 | Heath et al. | |
| 5,829,590 A | 11/1998 | Klein | |
| 6,158,437 A * | 12/2000 | Vagley .................. | A61C 19/02 128/898 |
| 6,719,560 B2 | 4/2004 | Capt | |
| 7,527,147 B2 | 5/2009 | Corcoran et al. | |
| 8,157,090 B2 * | 4/2012 | Ingvardsen ............ | B25H 3/026 206/315.9 |
| 2007/0138042 A1 | 6/2007 | Wood | |
| 2008/0166682 A1 | 7/2008 | Bjorn et al. | |
| 2010/0065456 A1 | 3/2010 | Junk et al. | |
| 2010/0320162 A1* | 12/2010 | Kao ........................ | B25H 3/04 211/70.6 |
| 2012/0138495 A1 | 6/2012 | Bettenhausen et al. | |
| 2014/0202903 A1 | 7/2014 | Dassonville et al. | |

* cited by examiner

MEDICAL DEVICE TRAY AND METHOD OF FORMING THE MEDICAL DEVICE TRAY

CROSS REFERENCE TO RELATED APPLICATIONS

This is a continuation-in-part of U.S. patent application Ser. No. 14/157,811, entitled "MEDICAL DEVICE TRAY AND METHOD OF FORMING THE MEDICAL DEVICE TRAY," filed Jan. 17, 2014, pending which is incorporated herein by reference.

BACKGROUND OF THE INVENTION

1. Field of the Invention

The present invention relates to trays, and, more particularly, to medical device trays.

2. Description of the Related Art

A surgical tool container system is known which can hold surgical tools for purposes of organization and sterilization. Such a system includes a tool holding tray with a plurality of holes. Elastomeric grommets are fixedly secured within a respective hole to removably secure surgical tools to the tray. A disadvantage of using such grommets is that the grommets can be difficult to sterilize.

Dental trays, for example, can be used to hold dental devices. By using such a tray, the dental devices are stored on the tray in an organized manner, which helps the dentist to quickly identify the proper device during a dental procedure. A dental tray is known which uses individually positioned grommets (for example, silicone rivets) or inserts to hold dental devices (for example, dental instruments) in the dental tray. The individual grommets are difficult to clean and sterilize. There is the possibility that blood and organic particulate matter may be trapped in the grommets. For example, grommets assembled in radel or metal trays present areas where biological contaminants, such as dried blood or tissues could be trapped; these contaminants are difficult to remove during cleaning and sterilization.

What is needed in the art is a medical device tray that is simple in design and relatively easy to sterilize.

SUMMARY OF THE INVENTION

The present invention provides a medical device tray that does not use grommets or inserts to hold the dental devices.

The invention in one form is directed to a medical device tray for carrying a plurality of medical devices. The medical device tray includes: a base made of a substantially rigid material, the base forming at least one base through-hole, the at least one base through-hole having an associated visual indicator; and a covering affixed to the base, the covering being made of a material which is softer than the substantially rigid material of the base and substantially transparent, the covering forming at least one covering through-hole, the at least one base through-hole and the at least one covering through-hole cooperating to form at least one medical device tray through-hole configured for directly supporting a respective one of the plurality of medical devices.

The invention in another form is directed to a medical device tray system. The medical device tray system includes: a medical device; and a medical device tray configured for carrying a plurality of the medical device. The medical device tray includes: a base made of a substantially rigid material, the base forming at least one base through-hole, the at least one base through-hole having an associated visual indicator; and a covering affixed to the base, the covering being made of a material which is softer than the substantially rigid material of the base and substantially transparent, the covering forming at least one covering through-hole, the at least one base through-hole and the at least one covering through-hole cooperating to form at least one medical device tray through-hole directly supporting the medical device.

The invention in yet another form is directed to a method of forming a medical device tray for carrying a plurality of medical devices. The method includes the steps of: providing a base made of a substantially rigid material, the base forming at least one base through-hole; forming a visual indicator on the base adjacent to the at least one base through-hole; affixing a covering to the base, the covering being made of a material which is softer than the substantially rigid material of the base and substantially transparent, the covering forming at least one covering through-hole, the at least one base through-hole and the at least one covering through-hole cooperating to form at least one medical device tray through-hole; supporting directly a respective one of the plurality of medical devices.

An advantage of the present invention is that it eliminates the individual grommets, thereby reducing the undercuts and corners where blood and/or other organic particulate matter may be trapped.

Another advantage is of the present invention is that it provides a simple and low cost method of reducing the biological contamination risks associated with surgical instrument trays (for example, but not limited to, dental surgery trays). The present invention is thus advantageous technically and from a cost point-of-view over a design that uses grommets.

Yet another advantage of the present advantage is that the visual indicators associated with the through-holes can be seen through and protected by the covering, which can extend the lifetime of the visual indicators.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION OF THE INVENTION

Figure 1:
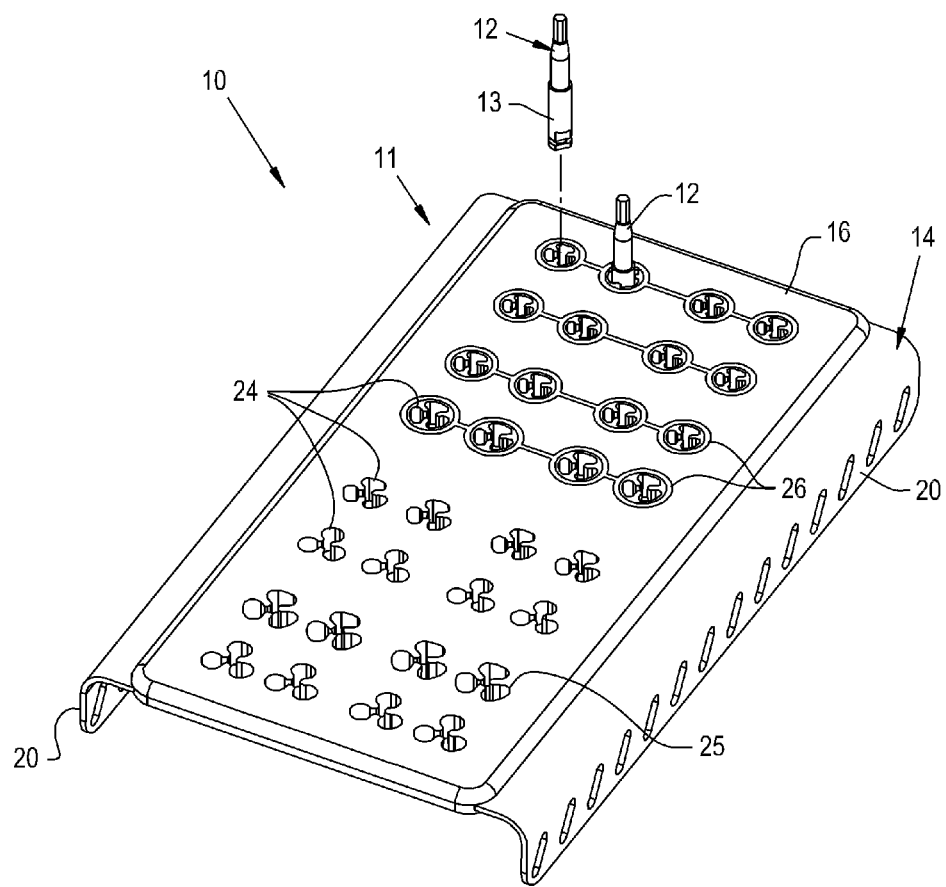
FIG. 1 is a perspective view of a dental tray system according to the present invention.
Figure 2:
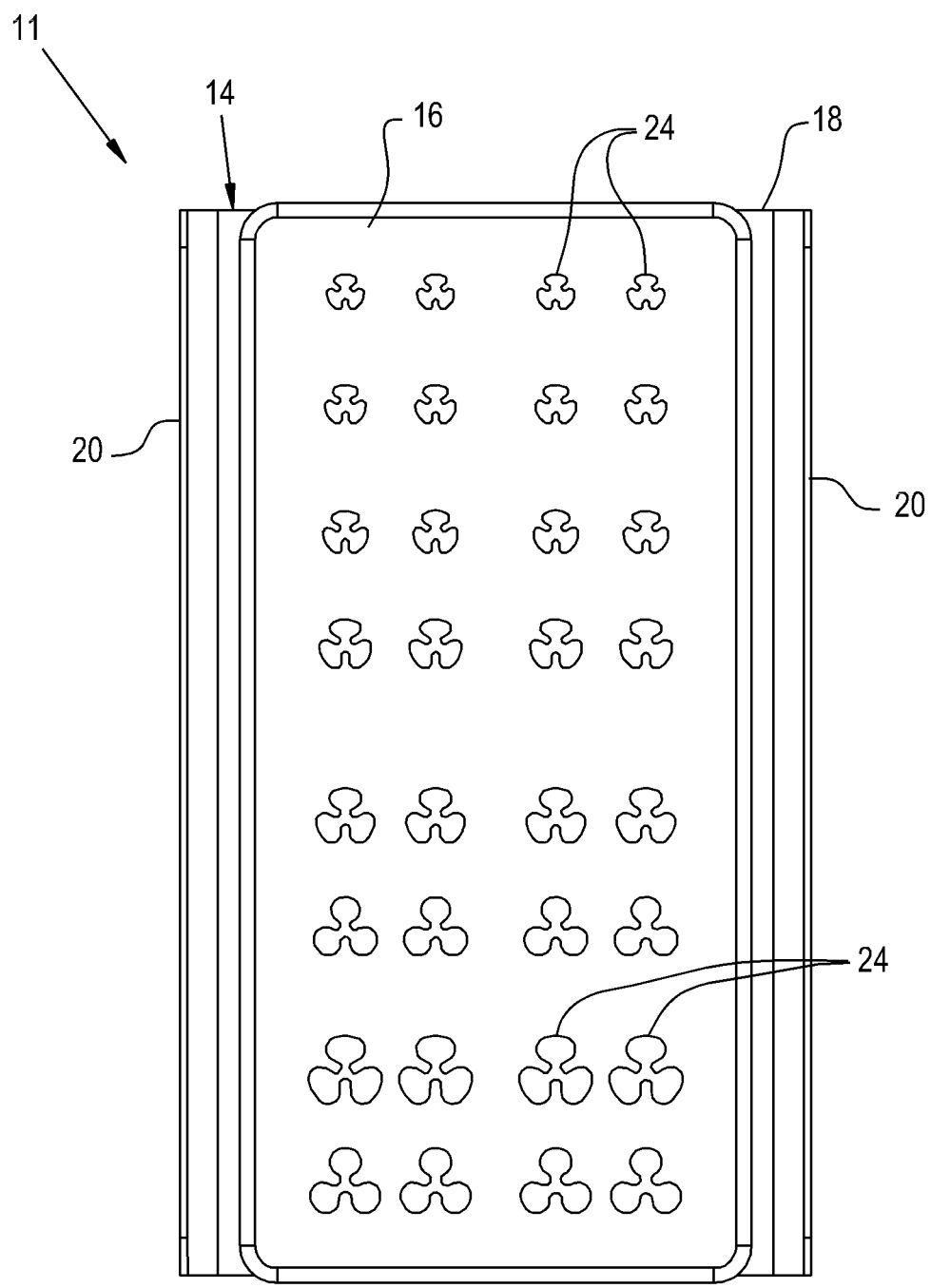
FIG. 2 is a bottom view of the dental tray of the dental tray system of FIG. 1.
Figure 3:
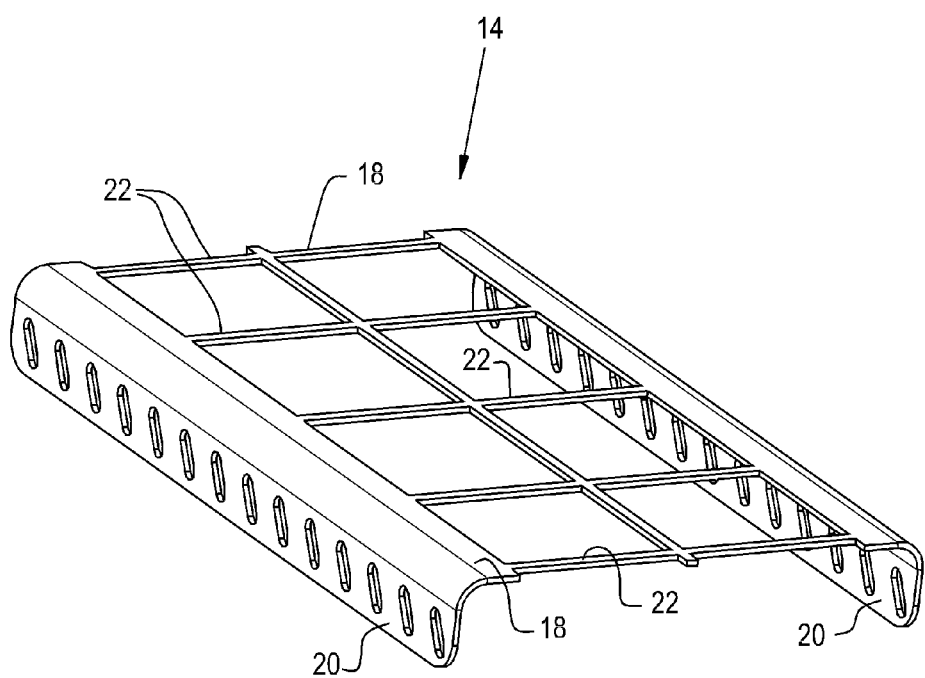
FIG. 3 is a perspective view of the base of the dental tray of FIG. 1.

Referring now to the drawings, and more particularly to FIGS. 1-3, there is shown, according to one embodiment of the present invention, a medical device tray system 10 which generally includes a medical device tray 11 and a medical device 12. Medical device tray 11 is configured for carrying a plurality of medical devices 12.

The medical device tray of the present invention has application to virtually any medical field. In other words, the medical device tray of the present invention (for example, medical device tray 11) can be used to carry medical devices used in medical procedures concerning teeth, feet, hands, shoulders, the spine, or virtually any other part of a corporeal body. Further, the medical device tray and the medical device of the present invention can be respectively a tray and a device used for medical procedures concerning human beings or for veterinary procedures (for animals). Further, the medical devices of the present invention can be implants, tools, implements, instruments, or virtually any medical device that can be carried by a tray; such medical devices include, for example, small medical instruments. By way of example and not by way of limitation, the description that follows describes an exemplary application of the present invention. That is, the medical device tray system, the medical device tray, and the medical device described herein is applied to the medical field of dentistry. Thus, the medical device tray system, the medical device tray, and the medical device described herein are, respectively, a dental tray system, a dental device, and a dental device. Thus, according to one embodiment of the present invention, medical device tray system 10, medical device tray 11, and medical device 12 are, respectively, dental tray system 10, dental tray 11, and dental device 12. However, as indicated, the present invention is not limited to the field of dentistry.

Thus, FIGS. 1-3 show, according to one embodiment of the present invention, dental tray system 10 which generally includes dental tray and dental device 12. Dental tray 11 is configured for carrying a plurality of dental devices 12. Dental tray 11 generally includes a base 14 and a covering 16 affixed to base 14. Dental tray 11 can be used by a dental or dental assistant during a dental procedure.

Dental device 12 can be various dental devices which are used in dental procedures and which can be held in a dental tray. These dental instruments can be relatively small. For example, the dental device held by the dental tray of the present invention can be, for example, a drill, a screwdriver, an awl, a dental burr, or another device; these examples are provided by way of example and not by way of limitation. Two dental devices 12 are shown in FIG. 1; both dental devices are the same in size and shape. One dental device 12 in FIG. 1 is exploded from dental tray 11, and the other dental device 12 is shown positioned in a hole (covering through-hole 24) in dental tray 11. Dental device 12 shown in FIG. 1 is a hex screwdriver, the hexagonal head being at the top of the device shown in FIG. 1 (dental device 12 is not shown in FIG. 2). Dental device 12, as shown in FIG. 1, includes a dental adapter 13. Covering 16 of dental tray 11 (in particular, the silicone, for example, of covering 16) can hold dental device 12. For example, the internal diameter of covering 16 (at a covering through-hole 24) can be water jet cut to approximately 1.66 mm, and dental adapter can have a diameter of 2.35 mm; in this way, an interference between the material of cover 16 (such as silicone) and dental device 12 ensures that cover 16 holds dental device 12 (by way of an interference fit) and prevents dental device 12 from falling through covering through-hole 24. This dimension of covering through-hole 24 can be taken from either the outer radius of covering through-hole 24 (the outer radius being the widest radius of covering through-hole 24) or the inner radius of covering through-hole 24 (the inner radius being taken from where the radially inner tips of the projections forming through-hole 24 project inwardly, cover through-holes 24 in FIG. 1 having essentially three such inwardly extending projections). These dimensions, and this means of holding, are provided as merely one example and are thus not provided by way of limitation. The cutout shown at the bottom of dental device 12 in FIG. 1 is also an adapter that allows dental device 12 to be attached to a motor or to a handle. The material of dental device 12 can be stainless steel (adapter 13 can also be stainless steel or can be another material, such as a resilient material).

Base 14 of dental tray 11 is made of a substantially rigid material. In this way, base 14 provides a stable structure that can be placed on a table for instance; base 14 provides rigidity for dental tray 11. The substantially rigid material of base 14 can metallic, plastic, another material sheet to guarantee rigidity, or another rigid material. If metal is used, the material can be, for example, stainless steel, such as medical grade stainless steel; this material is provided by way of example and not by way of limitation. Base 14 can be formed by molding, machining, stamping, pressing, bending, and/or any other suitable method. FIG. 3 shows that base 14 includes a central frame 18 and two legs 20 depending downwardly from central frame 18.

FIG. 3 shows one embodiment of base 14 according to the present invention, base 14 being shown by itself and thus without covering 16. As shown in FIG. 3, base 14 forms at least one base through-hole 22. FIG. 3 shows that central frame 18 can include a plurality of base through-holes 22. FIG. 3 shows eight such base through-holes 22, but more or less such base through-holes 22 can be used. Each leg 20 depends from a longitudinal side of central frame 18; each leg 20 can include, for example, a plurality of through-holes, as shown in FIGS. 1 and 3. Base 14 can be considered a plate 14.

Covering 16 of dental tray 11 is made of a material which is softer than the substantially rigid material of base 14. The material of covering 16 can be a biocompatible soft material, such as silicone, santoprene, or another suitable material; this material is provided by way of example and not by way of limitation. According to one embodiment of the present invention (such as the embodiment shown in FIGS. 1-3), covering 16 is formed by injection molding. More specifically, according to this embodiment of the present invention, covering 16 is overmolded onto base 14, in particular, over central frame 18 of base 14. Stated another way, the step of affixing includes injection molding a material of covering 16 and thereby overmolding covering 16 onto base 14. Thus, for example, the stainless steel plate 14 (the base 14) can be overmolded with silicone to form covering 16 on base 14. Covering 16 forms at least one covering through-hole 24. FIGS. 1 and 2 show that covering 16 includes several such covering through-holes 24. Covering through-holes 24 can be substantially perpendicular to the top and bottom surfaces of covering 16. For instance, FIGS. 1 and 2 show that covering 16 can include eight rows of four such covering through-holes 24. According to one design example, covering through-holes 24 at one longitudinal end of dental tray 11 can be smaller than covering through-holes 24 at the other longitudinal end of dental tray 11 (this is shown in the drawings). After overmolding covering 16 over central frame 18 of base 14, covering through-holes 24 can be cut into covering 16 (central frame 18 already has eight large holes 22). Covering through-holes 24 can be formed by, for example, a water jet (by water jet cutting), a laser (by laser cutting), or another suitable process. These methods of cutting are provided by way of example and not by way of limitation. Thus, the method of the present invention can include cutting at least one covering through-hole 24 in covering 16 by water jet cutting or laser cutting. Through-holes 24 cut into covering 16 thus form features configured for holding the dental devices 12, such as dental surgery instruments. These holes 24 in the covering 16 are thus through-holes 24 which allow the dental devices 12 to extend through the overmolded covering 16. These holes 24 can be formed such that they are perpendicular to both the top side and the bottom side of the covering 16. FIG. 3 shows that base 14 of one embodiment includes eight base through-holes 22 formed in central frame 18 of base 14. Each of these base through-holes 22 is rather large compared to each one of covering through-holes 24 in FIGS. 1 and 2; thus, a plurality of covering through-holes 24 are associated with a respective one of base through-holes 22 (for example, comparing FIGS. 2 and 3, four such covering through-holes 24 can be associated respectively with each base through-hole 22).

The overmolding operation provides that each base through-hole 22 is filled by the material of covering 16. Stated another way, the material of covering 16 flows over central frame 18 and bonds (or becomes otherwise affixed) thereto and is shaped by the mold to fill the spaces 22 (the base through-holes 22) formed by central frame 18. Thus, base through-hole 22 is filled by covering 16 and includes therethrough the plurality of covering through-holes 24 which define a plurality of dental tray through-holes 25 (which, as indicated above, can more generally be referred to as medical device tray through-holes 25). A respective base through-hole 22 includes a plurality of covering through-holes 24 in the sense that such covering through-holes 24 extend through the material of covering 16, this covering material being positioned in and thereby filling this respective base through-hole 22. In this way, at least one base through-hole 22 and at least one covering through-hole 24 cooperate with one another to form at least one dental tray through-hole 25 (which can more generally be referred to as medical device tray through-hole 25) configured for directly supporting a respective one of the plurality of dental devices 12 (which can more generally be referred to as medical devices 12). FIG. 1 shows dental tray through-hole 25 directly supporting dental device 12. With reference to the embodiment of the dental tray 11 of the present invention shown in FIGS. 1-3, this cooperation thus occurs in the sense that the larger base through-hole 22 is filled with the covering material, and the covering material includes at least one covering through-hole 24 therethrough which is positioned in this larger base through-hole 22; in this way, a respective covering through-hole 24 alone forms the actual respective dental tray through-hole 25, and the covering through-holes 24 and the dental tray through-holes 25 are the same structure in this particular embodiment of the dental tray of the present invention. Further, the respective dental tray through-hole 25 supports the respective dental device 12 without using a grommet or insert to hold the dental device 12 in dental tray through-hole 25; in other words, dental tray 11 (which can be referred to as a medical device tray 11) has an absence of a grommet or insert which is configured for holding the respective one of the plurality of dental devices 12 (which can be referred to as a medical devices 12). Dental through-hole 25 receives and supports the respective dental device by way of, for example, an interference fit, a friction fit, or a widening section on the dental device which catches on the top surface of covering 16 and thereby prevents the dental device from "falling" through the respective dental through-hole 25 (these examples are provided merely by way of example and not by way of limitation). For example, in one embodiment, the diameter of adapter 13 can be larger than the inner radius (formed by the tips of the inwardly extending projections) of covering through-hole 24 (but smaller than the outer radius of covering through-hole 24) and be held by the radially inwardly extending projections of covering through-hole 24 by an interference fit. In this alternative, holes may exist radially outwardly of adapter 13 so that steam can travel upwardly through these holes between adapter 13 and covering through-hole 24 during cleaning and/or sterilizing processes. Alternatively, the diameter of adapter 13 can be slightly larger than the outer radius of covering through-hole 24 but can still be press fit into covering through-hole 24 to be held by covering through-hole 24 by an interference fit (for instance, due to the resilience of the material of covering 16).

After overmolding covering 16 over base 14 and cutting through-holes 24 in covering 16 to hold the dental devices 12 (i.e., dental instruments 12), covering 16 can be marked. That is, a marking 26 can be applied on the soft material of covering for purposes of color coding. FIG. 1 shows the top side of covering, the top side of covering being shown with circular markings 26 around four adjacent rows of covering through-holes 24. Each row of circular markings 26 can be a different color relative to the other rows of circular markings 26. For example, each of the circular markings 26 in the first row (the row having circular markings 26 and being nearest the transverse edge of dental tray 11) can be colored white. Each of the circular markings 26 in the second row can be colored red. Each of the circular markings 26 in the third row can be colored yellow. Each of the circular markings 26 in the fourth row can be colored blue. This arrangement of colors is provided by way of example and not by way of limitation. The purpose of the color coding is to help the dentist organize the dental devices 12 on the dental tray 11 into logical groupings. The color markings 26 can be placed on covering 16 by way of silk screen printing, for example; this process is provided by way of example and not by way of limitation. In this way, an ink marking (a respective color marking 26) can be printed on covering 16. After performing sterilization and detergent tests on some samples, the ink appeared to be resistant (resistant to being removed from the covering).

Figure 4:
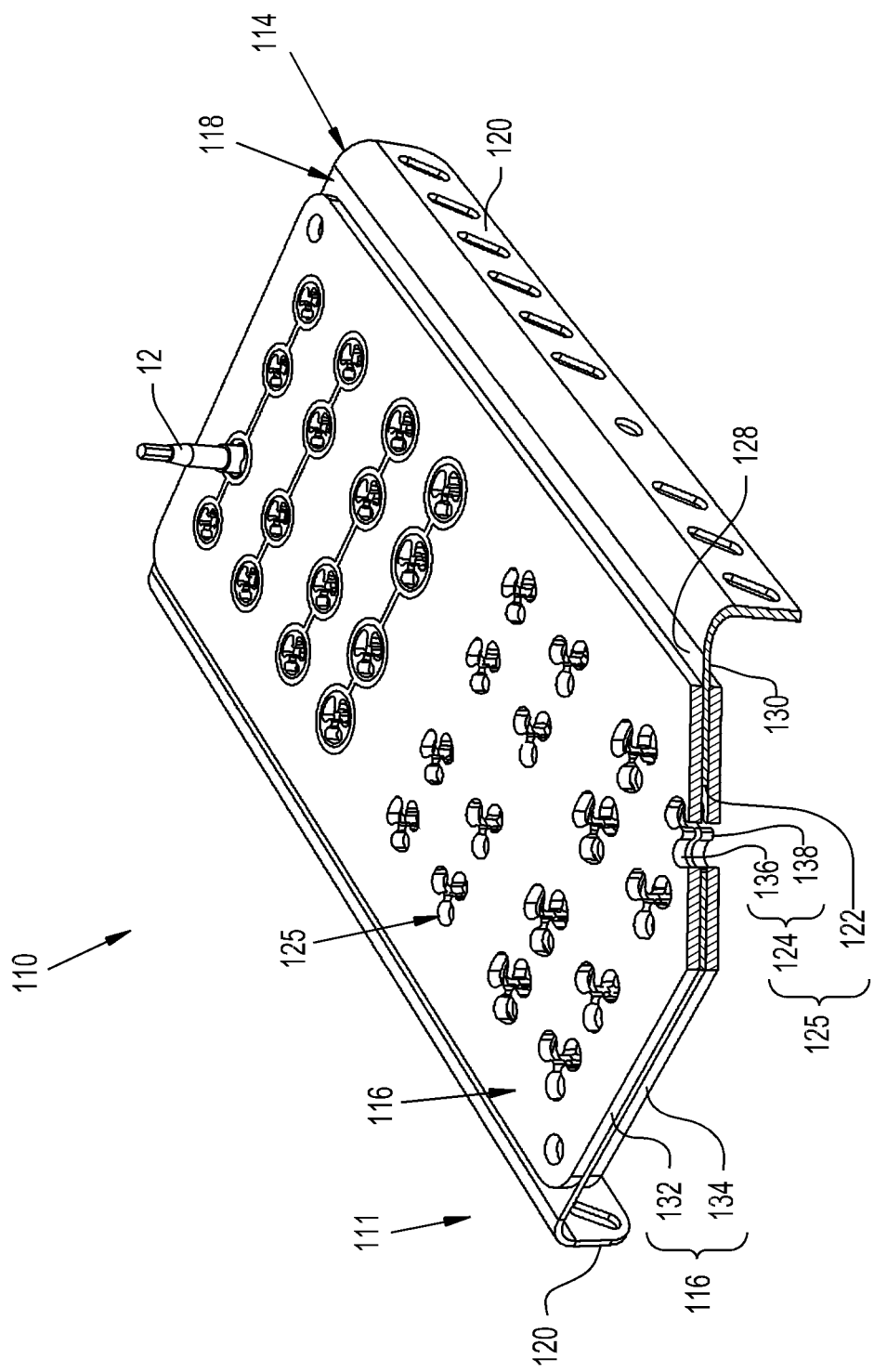
FIG. 4 is a perspective view of another embodiment of a dental tray system according to the present invention, with portions broken away.
Figure 5:
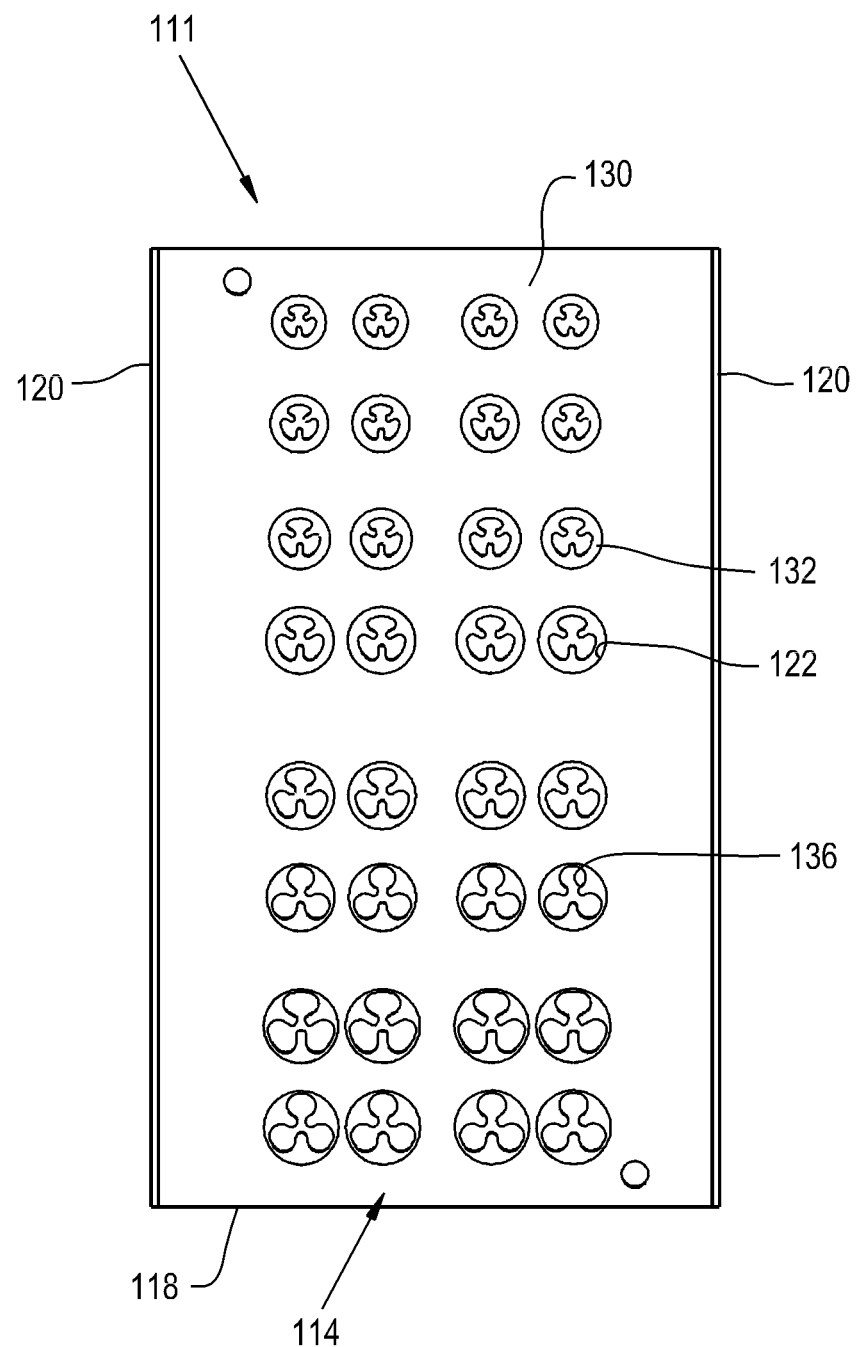
FIG. 5 is a bottom view of the dental tray of the dental tray system of FIG. 4, with portions broken away.

FIGS. 4 and 5 show another embodiment of the dental tray according to the present invention. The dental tray 111 of FIGS. 4-5 is similar to the dental tray 11 of FIGS. 1-3. Certain ones of the differences are highlighted herein. Structural elements in FIGS. 4-5 which are similar to that shown and described relative to the embodiment of FIGS. 1-3 are provided with a reference number raised by 100 relative to similar structures in FIGS. 1-3, even if the structures are not exactly identical. It is understood that a dental device 12 can be held in any one of the dental tray through-holes 125 of dental tray 111 and thereby form a dental system, similar to that described and shown with reference to FIGS. 1-3 (dental device is shown in FIG. 4 but not in FIG. 5). Dental system 110 includes dental tray 111 of FIGS. 4-5, dental tray 111 including base 114 and covering 116.

Base 114 can be made of the same material and in the same manner as described above relative to FIGS. 1-3. Base 114 includes central frame 118 and legs 120 depending from central frame 118. Central frame 118, however, has more material than the embodiment described above. Base through-holes 122 are generally circular through-holes. The size and shape of base through-holes 122 can vary from row-to-row or in any manner so desired. Further, FIGS. 4 and 5 show that two additional, smaller holes can be formed in central frame 118 at opposing corners. Central frame 118 of base 114 includes a top side 128 and a bottom side 130.

Covering 116 of FIGS. 4-5 can be made of the same material as described above relative to FIGS. 1-3. FIGS. 4-5 show that covering 116 includes a top layer 132 and a bottom layer 134. Each layer 132, 134 is substantially identical to one another. Top layer 132 is mounted to top side 128 of base 114. Bottom layer 134 is mounted to bottom side 130 of base 114. In this way, as shown in FIG. 4, top and bottom layers 132, 134 of covering 116 sandwich central frame 118 of base 114. Top and bottom layers 132, 134 of covering 116 can be bonded to central frame 118 of base 114, such as by using an adhesive, such as silicone glue; this way of attachment is provided by way of example and not by way of limitation.

Covering 116 includes covering through-holes 124. Top layer 132 and bottom layer 134 can be considered two halves of covering 116. In this sense, each covering through-hole 124 has a first half 136 and a second half 138, first half 136 being formed by top layer 132, second half 138 being formed by bottom layer 134. Because top and bottom layers 132, 134 of covering 116 sandwich base 114, first and second halves 136, 138 of each covering through-hole 124 are spaced apart from one another but yet are considered to form together a respective covering through-hole 124. Top layer 132 includes first half 136 of at least one covering through-hole 124, and bottom layer 134 includes second half 138 of at least one covering through-hole 124. Thus, each layer 132, 134 has through-holes cut in substantially the same place as the other, these through-holes being cut in substantially the same size and shape relative to one another. In this way, first and second halves 136, 138 of at least one covering through-hole 124 are substantially aligned with one another. Further, first and second halves 136, 138 are positioned relative to at least one base through-hole 122 such that first half 136, second half 138, and at least one base through-hole 122 together form at least one dental tray through-hole 125 (which can be referred to as medical device tray through-hole 125). In this way, a respective base through-hole 122 and a respective covering through-hole 124 cooperate to form at least one dental tray through-hole 125 configured for directly supporting a respective one of the plurality of dental devices 12. Indeed, base through-hole 122 and covering through-hole 124 cooperate to form a dental tray through-hole 125 which directly supports a dental device 12. FIG. 5 shows a bottom view of dental tray but without bottom layer 134 of covering 116. Thus, FIG. 5 shows base 114, and portions of top layer 132 of covering 116 can be seen through base through-holes 122 in base 114. FIG. 5 thus shows that each base through-hole 122 has a radius which is as large as or larger than the outer radius of first half 136 of covering through-hole 124 formed in top layer 132 (the same is true relative to bottom layer 134). Because the material of top and bottom layers 132, 134 extend radially inwardly of base through-hole 122, a gap which is not filled by base 114 can be formed between top and bottom layer 132, 134.

Covering through-holes 122 (as well as the holes in legs 120 of base 114) can be formed in base 114 before layers 132, 134 of cover 116 are attached to base 114. First and second halves 136, 138 of covering through-holes 124 in top and bottom layers 132, 134 can be cut (as described above) either before layers 132, 134 are attached to base 114 or after layers 132, 134 are attached to base 114. Layers 132, 134 of covering 114 can be individually formed by molding (for example, injection molding), cutting from a blank, or another suitable method. First and second halves 136, 138 of covering through-holes 124, as well as base through-holes 122, can be substantially perpendicular to the top surface and the bottom surface of covering 116.

As stated above, dental through-hole 125 supports the respective dental device by way of, for example, an interference fit, a friction fit, or a widening section on the dental device which catches on the top surface of covering 116 and thereby prevents the dental device from "falling" through the respective dental through-hole 125 (these examples are provided merely by way of example and not by way of limitation). Further, the respective dental tray through-hole 125 receives and supports the respective dental device without using a grommet or insert to hold the dental device in dental tray through-hole 125; in other words, dental tray 111 (which can be referred to as a medical device tray 111) has an absence of a grommet or insert which is configured for holding the respective one of the plurality of dental devices (which can be referred to as a medical devices). Covering through-holes 124 can hold the dental device in a similar way to (and thus function similar to) what has been described relative to the embodiment shown in FIGS. 1-3.

Figure 6:
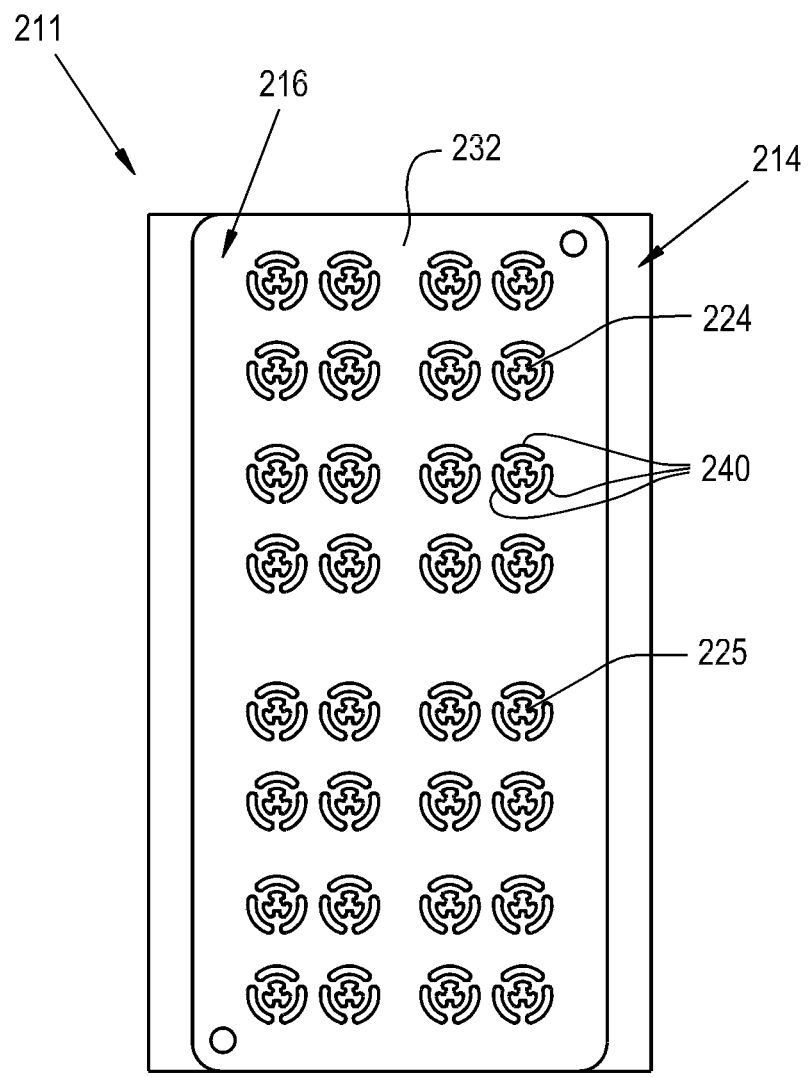
FIG. 6 is a top view of yet another embodiment of a dental tray according to the present invention.

FIG. 6 shows a top view of yet another embodiment of the dental tray according to the present invention. The dental tray of FIG. 6 is similar to the dental trays 11 and 111 of FIGS. 1-5. Certain ones of the differences are highlighted herein. Structural elements in FIG. 6 which are similar to that shown and described relative to the embodiment of FIGS. 1-3 are provided with a reference number raised by 200 relative to similar structures in FIGS. 1-3, even if the structures are not exactly identical. It is understood that a dental device 12 can be held in the dental through-hole 225 of dental tray 211 and thereby form a dental system, similar to that described and shown with reference to FIGS. 1-3. A dental device is not shown in FIG. 6.

Dental tray 211 includes base 214 and covering 216. Like covering 116, covering 216 has two layers, only top layer 232 being shown in FIG. 6. Covering 216 includes additional holes. Covering 216 includes holes 240. FIG. 6 shows holes 240 positioned radially outside of covering through-holes 224. Each layer of covering 216 includes holes 240, holes 240 in each layer being substantially aligned relative to one another. The radius of base through-holes (not shown in FIG. 6) is as large as or larger than an outer radius associated with holes 240 and running from the center of covering through-holes 224 to the radial outer extent of holes 240. In this way, an unobstructed path is created between holes 240 in the top and bottom layers of covering 216. Alternatively, base 214 can include similarly sized and shaped holes relative to holes 240 such that holes 240 in the top and bottom layers of covering 216 are substantially aligned with similar holes in base 214. The purpose of holes 240 is to allow steam to travel through dental tray 211, such as from the bottom of dental tray 211 to the top of dental tray 211; in this way, cleaning and sterilization of dental tray 211 can be improved. Covering through-holes 224 can hold the dental device in a similar way to (and thus function similar to) what has been described relative to the embodiment shown in FIGS. 1-5.

While not shown in the drawings, the dental tray of the present invention can be held, carried, transported, or otherwise supported in a container. The container has a base and a lid which pivots relative to the container base. The legs of the dental tray rest on the bottom of the container base. The lid can have through-holes therein to facilitate cleaning and/or sterilizing the dental tray contained therein.

Each of the embodiments of the dental tray of the present invention can be used essentially in the same manner. Thus, in use, the dental tray can be stored and/or transported in the container. The dental tray can either remain in the container or be removed from the container when used during a dental procedure by a dentist. For instance, the dental tray can be removed from the container and placed on a table or other platform used during a medical procedure. Either way, a dental device can be held directly by the through-holes through the covering and base of the dental tray without the need for a grommet or any other holding device inserted into the holes of the covering. Each of the holes can hold a dental device. The holes can be sized and/or shaped differently to hold different sorts of dental devices. The dental device can be inserted into a respective dental tray through-hole by inserting the dental device from the top of the dental tray.

According to the main purpose of the dental tray of the present invention, the dental tray is designed to eliminate the individual grommets and to erase any possibility (or at least to reduce the possibility) of potentially contaminated areas. According to a secondary purpose of the dental tray of the present invention, the dental tray can be designed to be compatible with sterilizing process machines. Further, according to design choice, the dental tray can be designed to be washing machine compatible such that dental instruments are fitted in (that is, present in) the tray during washing and sterilization. Further, according to design choice, the exact size and position of the contact points between the dental instruments and the soft material (the covering) can be optimized so as to ensure the correct flow of washing and sterilizing fluids through the dental tray.

The present invention further provides a method of forming a medical device tray 11, 111 for carrying a plurality of medical devices 12, 112. The method includes the steps of: providing a base 14, 114 made of a substantially rigid material, base 14, 114 forming at least one base through-hole 22, 122; affixing a covering 16, 116 to base 14, 114, covering 16, 116 being made of a material which is softer than the substantially rigid material of base 14, 114, covering 16, 116 forming at least one covering through-hole 24, 124, at least one base through-hole 22, 122 and at least one covering through-hole 24, 124 cooperating to form at least one medical device tray through-hole 25, 125; supporting directly a respective one of the plurality of dental devices 12, 112. The substantially rigid material of base 14, 114 is stainless steel. The material of covering 16, 116 is biocompatible and is silicone or santoprene. Medical device tray 11, 111 has an absence of a grommet configured for holding the respective one of the plurality of medical devices 12, 112. The step of affixing includes overmolding covering 16 onto base 14. The at least one covering through-hole 24 includes a plurality of covering through-hole 24, base through-hole 22 being filled by covering 16 and including therethrough the plurality of covering through-holes 24 which define a plurality of the at least one medical device tray through-hole 25. Base 114 includes a top side 128 and a bottom side 130, covering 116 including a top layer 132 and a bottom layer 134, top layer 132 being mounted to top side 128, bottom layer 134 being mounted to bottom side 130, top layer 134 including a first half 136 of the at least one covering through-hole 124, bottom layer 134 including a second half 138 of the at least one covering through-hole 124, first half 136 of the at least one covering through-hole 124 and second half 138 of the at least one covering through-hole 124 being substantially aligned with one another and positioned relative to the at least one base through-hole 122 such that first half 136, second half 138, and the at least one base through-hole 122 together form the at least one medical device tray through-hole 125. The step of affixing includes injection molding a material of covering 16 and thereby overmolding covering 16 onto base 14, the method further including cutting at least one covering through-hole 24 in covering 16 by water jet cutting or laser cutting. The method can further include printing an ink marking 26 on covering 16.

Figure 7:
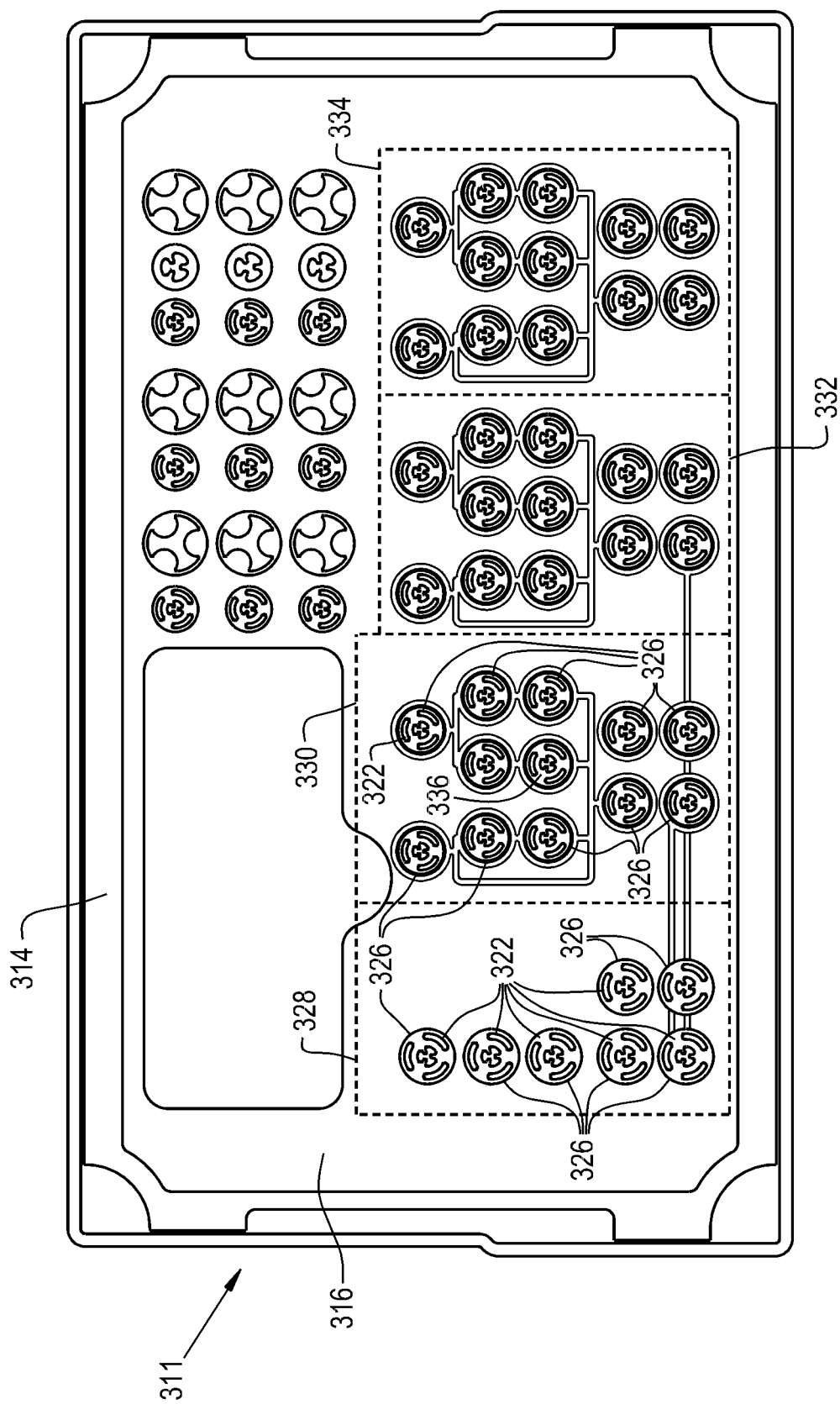
FIG. 7 is a perspective view of yet another embodiment of a dental tray according to the present invention.
Figure 8:
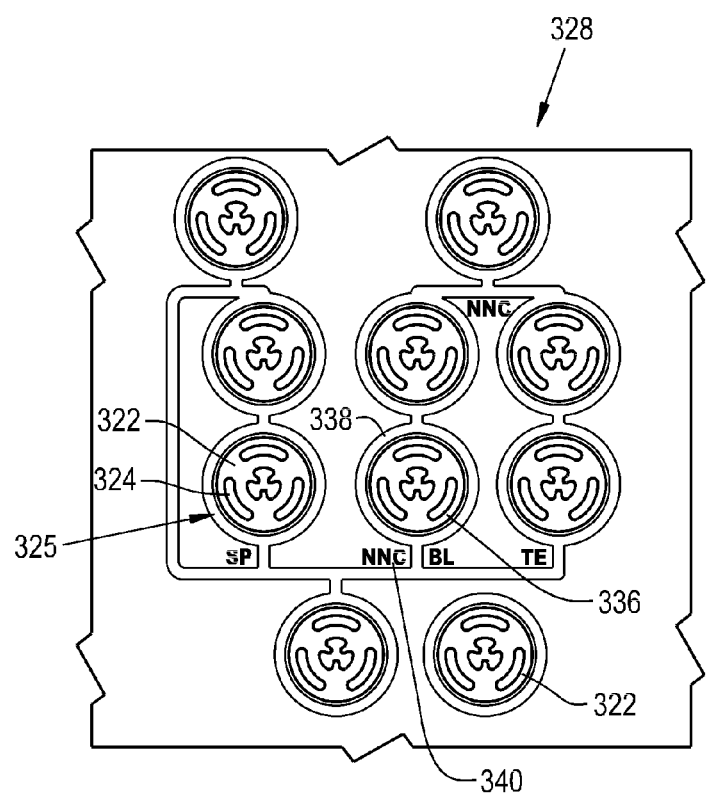
FIG. 8 is another perspective view of the dental tray shown in FIG. 7.

Referring now to FIGS. 7 and 8, a medical device tray 311 is shown that is similar to previously described medical device trays 11, 111 and 211. The medical device tray 311 includes a base 314 and covering 316 that is affixed to the base 314. The base 314 is comprised of a substantially rigid material, such as stainless steel, and has at least one base through-hole 322 formed through. Unlike previously described medical device trays 11, 111 and 211, the base 314 of medical device tray 311 has visual indicators 326 associated with at least one of the base through-holes 322 that are formed on the base 314. As used herein, "associated with" means that the visual indicator 326 is sufficiently close to its associated base through-hole 322 to relay some type of information about the base through-hole 322. Therefore, the visual indicator 326 will be in relatively close proximity to its associated base through-hole 322 so that a user viewing the medical device tray 311 can associate the visual indicator 326 with the associated base through-hole 322 and obtain some type of information indicated by the visual indicator 326. For example, the visual indicator could be a red marking that surrounds one or more base through-holes and indicates that any instruments held in the base through-hole(s) surrounded by red marking have already been used and are not clean. Such a configuration is merely an example of how a visual indicator 326 could be usefully included in the base 314 of the medical device tray 311. The visual indicator(s) 326 could take a variety of forms, including ink markings, notches, and indicating openings. Each form of visual indicator(s) 326 could also have a variety of shapes, colors and sizes. The shapes can include geometric shapes, letters, and words. In this regard, the examples given show that a wide variety of visual indicators can be applied to the base 314 and associated with base through-holes 322 to conveniently provide a user with information about the base through-hole(s) 322 or provide a convenient way to organize medical devices in the tray 311. As shown in FIG. 7, multiple base through-holes 322 can be arranged in through-hole groupings 328, 330, 332 and 334 to provide a convenient way of organizing medical devices in the tray 311. Each through-hole grouping 328, 330, 332 and 334 can have respective base through-holes 322 with similar associated visual indicators 326. For example, the visual indicators 326 in through-hole grouping 328 could all be formed as blue circles that surround an associated base through-opening. The blue circles could indicate that a medical device held in the associated base through-opening is clean and suitable for use. In addition to color, the similar visual indicators 326 of a through-hole grouping could have similar sizes, shapes and locations on the base 314.

As shown in FIG. 8, one or more base through-holes 322 could have multiple associated visual indicators 326 to differentiate between other base through-holes 322 in a through-hole grouping 328, 330, 332, 334. Base through-hole 336 in through-hole grouping 330, for example, has a visual indicator 338, shown as an ink circle, that surrounds base through-hole 336 as well as a nearby visual indicator 340, shown as inked letter coding. The combination of visual indicators 338 and 340 make it more convenient for a user to keep the same surgical instrument held within base through-hole 336 throughout a surgery.

A covering 316 is affixed to the base 314 in a similar fashion to previously described coverings 16, 116 and 216. Also similar to previously described coverings 16, 116 and 216, covering 316 has at least one covering through-hole 324 formed through that will cooperate with a base through-hole 322 to form a medical device tray through-hole 325 that will directly support a medical instrument during use of the tray 311. Since the covering 316 will be placed over the base 314, the material that forms that covering 316 should be substantially transparent so that the visual indicator(s) 326 formed on the base 314 can be seen through the covering 316. As used herein, "substantially transparent" does not mean "completely transparent," but transparent enough that the visual indicator(s) 326 formed on the base 314 can be seen through the covering 316 by a user. Substantially transparent silicone materials are known and could be used to form the covering 316, as well as other substantially transparent materials. Other than the material of the covering 316 being substantially transparent, the covering 316 is substantially similar to previously described coverings 16, 116 and 216.

To form the medical device tray 311, the previously described method of forming medical device trays 11 and 111 can be used with slight modification. The modification is adding the step of forming a visual indicator 326 on the base 314 adjacent to at least one base through-hole 322 and affixing the covering 316 made of a substantially transparent material to the base 314. The visual indicator(s) 326 can be applied by, e.g., printing an ink marking adjacent to the base through-hole 322, forming a notch adjacent to the base through-hole 322, forming an indicating opening adjacent to the base through-hole 322, etc. Printing an ink marking on the base 314 can be accomplished using a variety of known substrate printing techniques, such as screen printing, and forming a notch or opening on the base 314 can be accomplished using etching techniques, such as water jet and laser etching. Applying other types of visual indicators 326 to the base 314 can be done in a variety of known ways, so it should be appreciated that the previously described methods are exemplary only and not intended to be limiting.

Forming the visual indicator(s) 326 on the base 314 and then covering the base 314 with a substantially transparent covering 316 allows for the covering 316 to protect the visual indicator(s) 326 from being removed. This is especially useful when the visual indicator(s) 326 is an ink marking, as an ink marking on a substrate is usually quite thin and prone to being scratched off or removed by a sterilizing process, such as autoclaving. The covering 316 protecting the visual indicator(s) 326 can allow for the visual indicator(s) 326 to survive many uses and cycles of sterilization without being removed, extending the life of the visual indicator(s) 326 before needing to be re-applied.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A medical device tray for carrying a plurality of medical devices, said medical device tray comprising:
    a base made of a substantially rigid material, said base forming a plurality of base through-holes, said plurality of base through-holes each having an associated visual indicator;
    a covering affixed to said base and covering said associated visual indicators, said covering being made of a material which is softer than said substantially rigid material of said base and substantially transparent, said covering forming a plurality of covering through-holes, said plurality of base through-holes and said plurality of covering through-holes cooperating to form a plurality of medical device tray through-holes configured for directly supporting the plurality of medical devices.

2. The medical device tray of claim 1, wherein said substantially rigid material of said base is stainless steel, said material of said covering being biocompatible silicone.

3. The medical device tray of claim 1, wherein said visual indicator is at least one of an ink marking, a notch and an opening.

4. The medical device tray of claim 1, wherein said covering is overmolded onto said base.

5. The medical device of claim 1, wherein at least two of said plurality of base through-holes form a through-hole grouping, each base through-hole of said through-hole grouping having a similar associated visual indicator.

6. The medical device of claim 5, wherein each said similar associated visual indicator has at least one of a similar size, a similar shape, and a similar ink color.

7. A medical device tray system, said medical device system comprising:
    a plurality of medical devices;
    a medical device tray including:
        a base made of a substantially rigid material, said base forming a plurality of base through-holes, said plurality of base through-holes each having an associated visual indicator;
        a covering affixed to said base and covering said associated visual indicators, said covering being made of a material which is softer than said substantially rigid material of said base and substantially transparent, said covering forming a plurality of covering through-holes, said plurality of base through-holes and said plurality of covering through-holes cooperating to form a plurality of medical device tray through-holes directly supporting said plurality of medical devices.

8. The medical device tray system of claim 7, wherein said substantially rigid material of said base is stainless steel, said material of said covering being biocompatible silicone.

9. The medical device tray system of claim 7, wherein said visual indicator is at least one of an ink marking, a notch and an indicating opening.

10. The medical device tray system of claim 7, wherein said covering is overmolded onto said base.

11. The medical device tray system of claim 7, wherein at least two of said plurality of base through-holes form a through-hole grouping, each base through-hole of said through-hole grouping having a similar associated visual indicator.

12. The medical device tray system of claim 11, wherein each said similar associated visual indicator has at least one of a similar size, a similar shape, and a similar ink color.

* * * * *